(12) United States Patent
Frank et al.

(10) Patent No.: US 10,246,557 B2
(45) Date of Patent: Apr. 2, 2019

(54) PH SENSITIVE QUANTUM DOTS FOR USE AS CURE INDICATORS

(71) Applicant: The Boeing Company, Chicago, IL (US)

(72) Inventors: Katherine L. Frank, Charleston, SC (US); Andrew M. Zweig, St. Louis, MO (US)

(73) Assignee: THE BOEING COMPANY, Chicago, IL (US)

( * ) Notice: Subject to any disclaimer, the term of this patent is extended or adjusted under 35 U.S.C. 154(b) by 83 days.

(21) Appl. No.: 14/955,388

(22) Filed: Dec. 1, 2015

(65) Prior Publication Data

US 2017/0152349 A1    Jun. 1, 2017

(51) Int. Cl.
| | |
|---|---|
| *C08G 75/00* | (2006.01) |
| *C08G 75/14* | (2006.01) |
| *C08G 75/02* | (2016.01) |
| *G01N 21/80* | (2006.01) |
| *B82Y 30/00* | (2011.01) |

(52) U.S. Cl.
CPC ............ *C08G 75/14* (2013.01); *C08G 75/02* (2013.01); *G01N 21/80* (2013.01); *B82Y 30/00* (2013.01)

(58) Field of Classification Search
CPC .................................................... C08G 75/14
USPC ........................................................... 436/85
See application file for complete search history.

(56) References Cited

U.S. PATENT DOCUMENTS

| | | |
|---|---|---|
| 2,466,963 A | 4/1949 | Patrick et al. |
| 2,789,958 A | 4/1957 | Fettes et al. |
| 4,165,425 A | 8/1979 | Bertozzi |
| 5,610,243 A | 3/1997 | Vietti et al. |
| 6,509,418 B1 | 1/2003 | Zook et al. |
| 8,969,470 B1 * | 3/2015 | Li .................... G01N 21/6428 257/441 |

FOREIGN PATENT DOCUMENTS

| | | | |
|---|---|---|---|
| WO | 2013090988 A1 | 6/2013 | |
| WO | WO-2013090988 A1 * | 6/2013 | ........... C09K 3/1012 |

OTHER PUBLICATIONS

Xiaoge Hu and Xiaohu Gao "Silica-Polymer Dual Layer-Encapsulated Quantum Dots with Remarkable Stability" ACS Nano, 2010, 4 (10), pp. 6080-6086.*

(Continued)

*Primary Examiner* — Christine T Mui
*Assistant Examiner* — Emily R. Berkeley
(74) *Attorney, Agent, or Firm* — MH2 Technology Law Group LLP

(57) ABSTRACT

Disclosed is a curable sealant composition including: (i) a thiol-terminated prepolymer and/or monomers thereof, wherein the thiol-terminated prepolymer is a polythioether or a polysulfide; (ii) an "ene" crosslinker having a molecular weight of about 100 to about 5000; and (iii) a pH indicator molecule including a quantum dot functionalized with a pH-responsive ligand. Methods for determining a sufficient cure state of a composition by combining the thiol-terminated prepolymer and/or monomers thereof and the "ene" crosslinker with a pH indicator molecule, including a quantum dot functionalized with a pH-responsive ligand, and (ii) then subjecting a resultant mixture of (i) to curing conditions until the mixture changes its color are also disclosed.

20 Claims, 1 Drawing Sheet

(56) References Cited

OTHER PUBLICATIONS

Takashi Jin, Akira Sasaki, Masataka Kinjo and Jun Miyazaki "A quantum dot-based ratiometric pH sensor" Chem. Commun., 2010, 46, 2408-2410.*

Ibrahim Yildiz, Erhan Deniz, Bridgeen McCaughan, Stuart F. Cruickshank, John F. Callan, and Franc-isco M. Raymo "Hydrophilic CdSe—ZnS Core-Shell Quantum Dots with Reactive Functional Groups on Their Surface" Langmuir 2010, 26(13), 11503-11511 (Year: 2010).*

Tao Zeng, Yanxi Hu, Na Wang, Chuanqin Xia, Shoujian Li, Yan Zu, Lei Liu, Zhiyi Yao,b Yuliang Zhaoab and Hai-Chen Wu "Effects of different metal ions on the fluorescence of CdSe/ZnS quantum dots capped with various thiolate ligands" Phys.Chem. Chem. Phys., 2013, 15, 18710 (Year: 2013).*

Mayo et al., "The Peroxide Effect in the Addition of Reagents to Unsaturated Compounds and in Rearrangement Reactions", Chem. Rev., 27, 1940, pp. 351-412.

Peng et al., "Synthesis and Isolation of a Homodimer of Cadmium Selenide Nanocrystals", Angew. Chem., Int. Ed. Engl., 36, 1997, pp. 145-147.

Kuckling et al., "Preparation of Nanogels with Temperature-Responsive Core and pH-Responsive Arms by Photo-Cross-Linking", Langmuir, 18, 2002, pp. 4263-4269.

Amalvy et al., "Synthesis and Characterization of Novel pH-Responsive Microgels Based on Tertiary Amine Methacrylates", Langmuir, 20, 2004, pp. 8992-8999.

Hoyle et al., "Thiol-Enes: Chemistry of the Past with Promise for the Future", Polym. Chem., 42, 2004, pp. 5300-5338.

Li et al., "Fabrication of pH-Responsive Nanocomposites of Gold Nanoparticles/Poly(4-vinylpyridine)", Chem. Mater., 19, 2007, pp. 412-417.

Liu et al., "pH-Sensitive Photoluminescence of CdSe/ZnSe/ZnS Quantum Dots in Human Ovarian Cancer Cells", J. Phys. Chem., 111, 2007, pp. 2872-2878.

Stoll et al., "Photoelectrochemical Signal Chain Based on Quantum Dots on Gold-Sensitive to Superoxide Radicals in Solution", Biosensors and Bioelectronics, 24, 2008, pp. 260-265.

Wang et al., "Mercaptopyridine Surface-Functionalized CdTe Quantum Dots with Enhanced Raman Scattering Properties", J. Phys. Chem. C, 112, 2008, pp. 996-1000.

Frasco et al., "Semiconductor Quantum Dots in Chemical Sensors and Biosensors", Sensors, 9, 2009, pp. 7266-7286.

Hoyle et al., "Thiol-Ene Click Chemistry", Angew Chem. Int. Ed., 49, 2010, pp. 1540-1573.

Dennany et al., "Electrochemiluninescence (ECL) Sensing Properties of Water Soluble Core-Shell CdSe/ZnS Quantum Dots/Nafion Composite Films", J. Mater. Chem., 21, 2011, pp. 13984-13990.

Ruedas-Rama et al., "Fluorescent Nanoparticles for Intracellular Sensing: A Review", Analytica Chimica Acta, 751, 2012, pp. 1-23.

Shi et al., "Flocculation Behavior of a New Recyclable Flocculant Based on pH Responsive Tertiary Amine Starch Ether", Carbohydrate Polymers, 88, 2012, pp. 132-138.

Orte et al., "Fluorescence Lifetime Imaging Microscopy for the Detection of Intracellular pH with Quantum Dot Nanosensors", ACS NANO, 7, 2013, pp. 6387-6395.

Vasudevan et al., "Core-Shell Quantum Dots: Properties and Applications", Journal of Alloys and Compounds, 636, 2015, pp. 395-404.

Author Unknown, "Safety Data Sheet, SILQUEST A-1102 SILANE", Momentive, Version 1.1, Sep. 16, 2015, pp. 1-15.

Author Unknown, "Safety Data Sheet, SILQUEST A-187 SILANE", Momentive, Verision 1.0, Jun. 10, 2015, pp. 1-12.

Cramer et al., "Photopolymerizations of Thiol-Ene Polymers without Photoinitiators", Macromolecules, 35, 2002, pp. 5361-5365.

* cited by examiner

PH SENSITIVE QUANTUM DOTS FOR USE AS CURE INDICATORS

BACKGROUND

Sealants are used in many industry sectors including building and construction, mining and transport, e.g., in aircraft, automotive vehicles and marine craft. The physical and chemical properties of a sealant may be tuned through design of the sealant polymer chemistry and through the use of additives in the formulation to meet any desired performance requirements, e.g., to obtain suitable rheological properties for deployment, cure kinetics, bond strength to a substrate, mechanical properties and chemical resistance.

Among their use in a range of applications, sealants are particularly relevant for the construction of modern aircraft, for example, for sealing fasteners, for obtaining fluid-tight seals in fuel tanks and for pressure seals in joints or surrounding fasteners. Chemical resistance is a fundamental requirement of aircraft sealants since they may be exposed to chemicals such as jet fuel, hydraulic fluids and cleaning agents in service. Sealants that incorporate sulfur into a polymer backbone, such as in polysulfide and polythioether based sealant formulations, are known to provide suitable performance characteristics for many aerospace applications.

When polysulfides or polythioethers are mixed with a curing agent, sealant work life (i.e., the time during which the material can be applied) begins. Sealant work life ends when the properties of the sealant (such as its rheological properties) are no longer suitable for the application method. Variation in cure rate may increase or decrease work life and the time required to reach a tack free state (i.e., sealant is no longer sticky to touch) and ultimate hardness.

In terms of deployment of the sealant in a manufacturing environment, such as in the manufacture of an aircraft, this cure phenomena inevitably leads to application and scheduling complexity and hence implications for work flow and productivity. Having a simple and reliable indicator, which could provide a distinct visual signal, signifying the progress and/or the end of a cure, may shorten the time between application of sealant and the beginning of a re-work cycle as needed. This can reduce some work to a single shift, or allow secondary sealant work to be performed at earlier points on the production line when access (for the work and the inspection) is easier. However, the present indicator molecules, which degrade and change color from blue to white, for example, upon exposure to heat and/or UV are often difficult to observe due to the low contrast between the two colors. Additionally, the color change does not necessarily directly correlate to the extent of cure. Accordingly, there remains a desire in the art for an indicator molecule having a readily observable color change, which corresponds to the curing progress of a sealant composition.

BRIEF SUMMARY

The present disclosure is directed to a curable sealant composition including: (i) a thiol-terminated prepolymer and/or monomer thereof, wherein the thiol-terminated prepolymer is a polythioether or a polysulfide; (ii) an "ene" crosslinker having a molecular weight in a range of 100 to 5000; and (iii) a pH indicator molecule including a quantum dot functionalized with a pH-responsive ligand.

Also provided herein is a method for determining a sufficient cure state of a composition, which method includes: (i) combining a) at least one of a thiol-terminated prepolymer or a monomer thereof, (b) an "ene" crosslinker and (c) a pH indicator molecule comprising a quantum dot functionalized with a pH-responsive ligand; and (ii) subjecting a resultant mixture of (i) to a curing condition until the resultant mixture changes its color, (iii) comparing the change in color of the resultant mixture to a reference standard, wherein a sufficient cure state of the composition is indicated when the color of the resultant mixture is the same color as the reference standard, and wherein the thiol-terminated prepolymer is selected from the group consisting of a polythioether and a polysulfide, and wherein the "ene" crosslinker has a molecular weight of about 100 to about 5000.

Further areas of applicability of the present disclosure will become apparent from the detailed description provided hereinafter. It should be understood that the detailed description and specific examples, while indicating typical examples, are intended for purposes of illustration only and are not intended to limit the scope of the disclosure.

BRIEF DESCRIPTION OF THE DRAWING

The patent or application file contains at least one drawing executed in color. Copies of this patent or patent application publication with color drawing will be provided by the Office upon request and payment of the necessary fee.

DETAILED DESCRIPTION

Figure 1A:
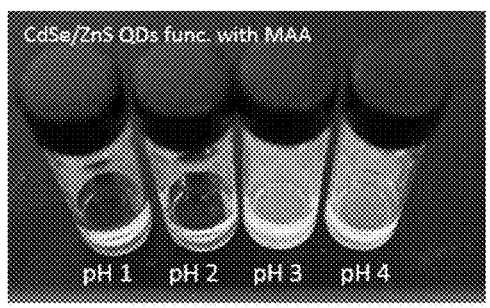
FIG. 1 depicts the fluorescence emission from CdSe/ZnS quantum dots functionalized with mercaptoacetic acid (MAA), FIG. 1A, or mercaptopropionic acid (MPA), FIG. 1B, at pH values ranging from 1 to 4.

The following description of the examples is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The present inventors have surprisingly recognized that a pH indicator molecule comprising a quantum dot functionalized with a pH-responsive ligand as described herein may be incorporated into a curable sealant composition and used to assess the extent of the cure of the composition after initiation of curing. During the curing process, the pH of a sealant composition comprising reactive acidic functional groups, e.g., SH groups, may change due to the consumption of these functional groups during polymerization (cure). Accordingly, the proton sources in the sealant composition are removed, changing the effective pH of the sealant composition during the curing process.

The inventors further recognized that quantum dots (QDs), which exhibit pH-responsive fluorescence when functionalized with pH-responsive ligands as reported in the literature, could be used to assess the progress and end point of a cure as the proton sources are removed during the cure. Furthermore, the inventors recognized that modified QDs could be efficaciously used to assess pH throughout the curing process since they are strong acid-base indicators, which are resistant to degradation by UV and shelf-stable. In addition, the fluorescence of QDs may be quenched at a decreased pH, for example, due to energy transfer between the QD and the pH-responsive ligand, allowing pH increases to be readily apparent. Further, large excitation windows and narrow fluorescence peaks make analysis simple and robust. Additional advantages of modified QDs for use as pH indicator molecules to assess curing of sealant compositions include a high fluorescence quantum yield and extinction coefficient allowing for bright dyes. In addition, tuning of the pH response may be readily accomplished via well established methods in synthetic chemistry.

Compositions

Thiol-Terminated Prepolymers and Monomers Thereof

The present disclosure is directed to a curable sealant composition including a pH indicator molecule as described herein. A "sealant" refers to a composition that can be used to form a connecting bond between two or more objects, articles or bodies or to fill at least a portion of any type of opening, junction or other space in, on or between one or more objects, articles or bodies (e.g. grooves, pits, cracks, joints, spaces between adjacent or overlapping members, pores, rivet holes and seams). Some sealants are used, for example, to fill a space defined by two or more overlapping or adjacent members of a structure, such as a joint connecting or between parts of an aircraft. In some examples, sealants can be used to smooth a surface or to act as a caulk-like material to slow or stop movement of moisture, chemicals, gases, debris, and other materials through or across an opening, junction or space.

In various examples, the present sealant compositions comprise thiol-terminated prepolymers and/or monomers thereof. The term "prepolymer" refers to a system of monomers that have been reacted to an intermediate molecular mass state. This material is capable of further polymerization by reactive groups to reach a fully cured high molecular weight state. As such, mixtures of reactive polymers with un-reacted monomers may also be referred to as prepolymers. The term "prepolymer" and "polymer precursor" may be used interchangeably herein. A "monomer" is a molecule that may bind chemically to other molecules to form a polymer.

As used herein, "thiol" refers to a mercaptan group, that is, an "SH" group bound to a carbon atom, A "thiol-terminated prepolymer" refers to a prepolymer comprising one or more terminal thiol groups that are reactive with other functional groups.

Polythioethers

In some examples, the thiol-terminated prepolymer is a polythioether having the following formula (I):

HS—R$^1$—[—S—(CH$_2$)$_p$—O—(—R$^2$—O—)$_m$—(CH$_2$)$_q$—S—R$^1$—]$_n$—SH    (I)

wherein R$^1$ is a C$_{2-10}$ n-alkylene, C$_{2-6}$ branched alkylene, C$_{6-8}$ cycloalkylene or C$_{6-10}$ alkylcycloalkylene group, heterocyclic, or —[(—CH$_2$)$_p$—X]$_q$—(—CH$_2$)$_r$—; or —[(—CH$_2$)$_p$—X]$_q$—(—CH$_2$)$_r$— in which at least one —CH$_2$— unit is substituted with a methyl group; R$^2$ is a C$_{2-10}$ n-alkylene, C$_{2-6}$ branched alkylene, C$_{6-8}$ cycloalkylene, C$_{6-10}$ alkylcycloalkylene group, heterocyclic, or —[(—CH$_2$)$_p$—X]$_q$—(—CH$_2$)$_r$;

X denotes one selected from the group consisting of O, S and —NR$^6$—;

R$^6$ denotes H or methyl;

m is independently selected from a value ranging from 1 to 50; and n is independently selected from a value ranging from 1 to 60;

p is independently selected from a value ranging from 2 to 6;

q is independently selected from a value ranging from 1 to 5; and r is independently selected from a value ranging from 2 to 10.

As is well understood by an ordinary artisan, polymers are mixtures of different molecular weight species. Accordingly, the ranges include fractional values, i.e., m, n, p, q, and r may be a fractional value of the integers specified above, e.g., m includes the values 4.8 and 6.3 as well as the integers 4 and 6.

In a more typical embodiment of the foregoing polymer, R$^1$ is C$_2$-C$_6$ alkyl and R$^2$ is C$_2$-C$_6$ alkyl.

In some examples, the present polythioether prepolymer is a difunctional thiol-terminated (uncapped) polythioether having the following structure:

HS—R$^1$—[—S—(CH$_2$)$_2$—O—[—R$^2$—O—]$_m$—(CH$_2$)$_2$—S—R$^1$—]$_n$—SH    (II)

In another typical embodiment, the present polythioether prepolymer has the formula R$^1$=—[(—CH$_2$)$_p$—X]$_q$—(—CH$_2$)$_r$—, where p=2, X=O, q=2 and r=2, R$^2$ is ethylene group, m=2 and n is about 9. In an alternative embodiment of the foregoing polythioether, when m=1 and R$^2$=n-butylene in formula II, R$^1$ is not ethylene or n-propylene. Also typically, when m=1, p=2, q=2, r=2 and R$^2$=ethylene, X is not O.

Other suitable polythioethers and methods for preparing polythioethers are well known in the art, e.g., as described in U.S. Pat. No. 6,509,418. More typically, however, the polythioethers for use in the present disclosure are prepared by reacting a suitable α,ω-dichloro-compound containing a formal group within its backbone, such as bis-2-chloroethyl formal, with sodium sulfide, sodium hydrosulfide, sodium tetrasulfide, sulfur or mixtures thereof in an emulsion in the presence of a strong base, e.g., sodium hydroxide. Typically, the use of a dichloro-compound during polythioether preparation will yield a linear polymer depending upon, among other factors, the stoichiometry of the starting materials, the reaction conditions and the further steps taken in subsequent processing.

In some examples, the presence of sulfur and sodium tetrasulfide in the polythioether reaction results in high molecular weight polymers. Further, the sulfur and sodium tetrasulfide introduce disulfides, tri-sulfides and tetrasulfides into the backbone of the molecule.

Reduction of a portion of the di-, tri- and tetrasulfides results in lower species which are thiol-terminated. To create a thiol-terminated polymer that has functionality greater than two, i.e., is capable of being crosslinked into a thermoset material, a tri-chloro species may be introduced into the reaction, e.g., 1,2,3-trichloropropane or related compounds. The proportion of such a trichloro species, as well as the timing of its introduction, may contribute to the distribution of molecular weight species as well as to the final average functionality.

As is well recognized by an ordinary artisan, some, but not necessarily all, of the molecules may be tri-functional or even higher. Further processing, such as that previously described, may also be applied to these higher functionality species to make useful resins for further reactions. It is also understood that while examples of chloro-compounds have been mentioned, the chloro groups simply serve as a "leaving group" in a bimolecular nucleophilic substitution reaction. Accordingly, leaving groups may include, but are not limited to bromo-, iodo-, tosyl- and the like, which are all well-known to those of ordinary skill in the art. Without being limited by theory, it is believed that the value of the polythioether polymers containing a formal linkage results in the suppression of the glass transition temperature of the final polymer. This property allows for a rubbery character at low temperature, a desirable feature in sealants.

Polysulfides

In some embodiments, the present sealant compositions may comprise polysulfides, e.g., linear or branched polysulfides. Methods for preparing suitable polysulfides are well known in the art and are described, for example, in U.S. Pat. Nos. 2,466,963, 2,789,958 and 4,165,425. Typically, suitable polysulfides are prepared by condensing sodium polysulfide with bis-(2-chloroethyl) formal in aqueous suspension. Suitable branched polysulfides may be prepared by introducing up to about 2 mole percent of trichloropropane along with the bis-(2-chloroethyl) formal. The interspersal of —SCH$_2$CH(SH)CH$_2$S— groups engendered by the trichloropropane provides for crosslinking when desired. The general structure of suitable linear and branched polysulfides is depicted by the following formula:

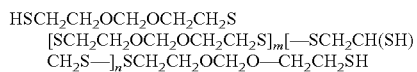
HSCH$_2$CH$_2$OCH$_2$OCH$_2$CH$_2$S
[SCH$_2$CH$_2$OCH$_2$OCH$_2$CH$_2$S]$_m$[—SCH$_2$CH(SH)
CH$_2$S—]$_n$SCH$_2$CH$_2$OCH$_2$O—CH$_2$CH$_2$SH wherein m is from about 5 to about 50, n is from 0 to about 1 and n/m is from about 0.002 to about 0.02, when greater than 0.

More typically, the present sealant compositions comprise a polysulfide that is a THIKOL® polysulfide having the following general formula:

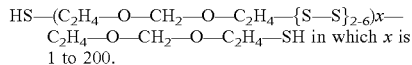
HS—(C$_2$H$_4$—O—CH$_2$—O—C$_2$H$_4$—{S—S}$_{2-6}$)x—
C$_2$H$_4$—O—CH$_2$—O—C$_2$H$_4$—SH in which x is
1 to 200.

Other suitable commercially available polysulfides are available under the trade name THIOPLAST™ G 21 from Akzo Nobel. Further, suitable polysulfides are also described in U.S. Pat. Nos. 2,466,963 and 5,610,243 and PCT Publication No. WO 2013/090988

The present thiol-terminated prepolymers and/or monomers thereof, such as the instant polythioether or polysulfide prepolymers and monomers thereof, may be present in an amount of up to about 99% based on the total weight of the formulation. It will be appreciated that this amount will vary depending on the amount of reinforcements and/or fillers and other additives present in the formulation.

Typically, sealants for aerospace applications contain between about 20 and about 40 percent by weight of fillers. The purpose of fillers is to improve the hardness; increase the tensile strength; decrease fluid absorption (e.g. fuel, water, hydraulic fluid); modify viscosity and related properties such as extrusion rate, slump, and sag; and reduce cost. Examples include, but are not limited to, mineral fillers such as clay, talc, and calcium carbonate; processed inorganic fillers such as fumed silica and carbon black; organic fillers such as plasticizers, solvents, stabilizers, cure accelerators, cure retardants, adhesion promoters (e.g. modified silanes or siloxy compounds); and other stabilizers and preservatives.

An ordinary skilled formulator will be able to adjust the total amounts as well as the relative amounts of these various additives to achieve the desired set of properties. For example, the addition of fumed silica will increase the viscosity of the sealant by its ability to form temporary and weak bonds between particles. This increases the viscosity when no shear force is applied, reducing the tendency for applied sealant to flow due to gravity (e.g. applied to a vertical surface or overhead). The same additive will increase the overall viscosity. Accordingly, a combination of additives to adjust the balance between the desired amount of flow for application and undesired flow after application may be suitably used.

In some examples, the present curable sealant compositions further include one or more non-polysulfide or non-polythioether prepolymer(s) and/or monomer(s). Non-limiting examples of non-polysulfide or non-polythioether prepolymers include polyamides and phenolic resins. Further non-limiting examples of non-polysulfide or non-polythioether monomer(s) include silane derivatives, such as is γ-aminopropyl-triethoxysilane (e.g., SILQUEST® A-1102, Momentive Corporation, Waterford, N.Y.), γ-glycidoxypropyl trimethoxysilane (e.g., SILQUEST® A-187, Momentive Corporation) and diglycidyl derivatives such as bisphenol A diglycidyl ether.

Curing

The present sealant compositions are "curable." As used herein, "curable" refers to compositions comprising any prepolymer and/or monomer that has at least one curable functional group, e.g. the terminal thiols of the present prepolymers and monomers thereof, which are able to crosslink during a curing process to yield a polymer. Curing may be accomplished by any art-known method. For example, an ordinary artisan recognizes that thiols can participate in at least four types of curing reactions. These include 1) oxidation reactions with manganese dioxide or other oxidants, 2) addition to carbon-carbon double bonds, also known as olefins, alkenes, i.e., "enes" as further described herein below, 3) ring-opening reactions with epoxy resins such as the glycidyl ether of bisphenol A, bisphenol F, and the like, and 4) exchange reactions with disulfides, which are found, for example, in commercial polysulfide resins. A variation of the fourth type is a reaction with elemental sulfur which is commonly used on commercial polysulfide resins in which sulfides react with sulfur to create disulfides, tri-sulfides and higher order or "rank" sulfides. See "Polyethers, Part III. Polyalkylene Sulfides and Other Polythioethers," Norman G. Gaylord, Editor, Interscience Publishers, New York, 1962, In some examples, polysulfide and/or polythioether based sealants may be formulated to cure at room temperature through the use of curing agents, such as manganese dioxide and lead oxide which convert the thiol end groups to sulfide based linkages. Chlorates, dichromates and organic and inorganic peroxides have also been employed for this purpose.

In more typical examples, cure of the present sealant compositions is facilitated through a source of unsaturation such as double or triple bonds, which may be carbon based with the crosslinked structure manipulated through the use of mono-, di-, tri- and/or tetra-unsaturated functional species as described in PCT Publication No. WO 2013/090988. Without being limited by theory, the general cure is based on thiol-ene chemistries. In various examples, the source of unsaturation is a double bond "ene" crosslinker having a molecular weight in the range of about 100 to about 5000, typically about 100 to about 1000. Examples include vinyl compounds such as diethylene glycol divinyl ether (DE-GDVE) (Mw=158), 1,4-cyclohexanedimethanol divinyl ether (Mw=196) and 1,3,5-triallyl-1,3,5-triazine-2,4,6(1H, 3H,5H)-trione (Mw=249). Other suitable "ene" crosslinkers include acrylate compounds such as 1,4-butanediol diacrylate (Mw=198), bisphenol A bimethacrylate (Mw=364), 1,3,5-triacryloylhexahydro-1,3,5-triazine (Mw=249) and pentaerythritol tetraacrylate (Mw=352).

When polysulfide sealants are to be cured, it has been found that the thiol-ene mole ratio has an impact on curing and the cross-linked network structure following exposure to a cure initiator as described herein. Typically, the ene component ranges from 0.7 to 1.5 moles per mole of thiol. More typically, the ene component ranges from 0.95 to 1.1 per mole of thiol. Most typically, the thiol-ene mole ratio is 1:1.

In some examples, a light trigger initiates cure of the sealant formulation. The light curing process is based on a photochemical reaction (photopolymerization). Photopolymerization of thiols with olefins, or "enes" has been known in the art since the early 20$^{th}$ century. See, for example, Mayo et al., *Chem. Rev.,* 1940, 27:351-412. See also Cramer et al., *Macromolecules,* 2002, 35:351-412. In some embodiments, light curing is desirable because it may be faster and more convenient than other curing methods. Typically, polymerization occurs in a few seconds to a few minutes without the need for high temperatures, solvents or complex equipment. However, elevated temperatures may be used, if desired, to cure a part of the present sealant composition, which cannot be cured with light curing due to "shadowing" issues, e.g., when light is unlikely to penetrate a depth of a slab.

In some examples, the light trigger may include light from the ultraviolet (184 to 254 nm), visible (390 nm-700 nm) or near infrared spectral ranges (750 nm to 950 nm). Examples of suitable light sources, which may be used with the present disclosure, include those available commercially from suppliers such as Fusion Systems Inc., Gaithersburg, Md.

As is understood by an ordinary artisan, the mechanism of curing initiation may vary depending on the wavelength of light used for curing, the thickness of the sample, the presence or absence of an acid or base and the concentration of oxygen in the formulation. In some examples, short wavelengths are used to initiate cure. Without being limited by theory, short wavelengths are believed to typically result in homolytic cleavage of the S—H bond creating thiyl radicals, which initiate the polymerization. Additionally, the use of short wavelengths, such as UV, typically creates a range of reactive intermediate species, which can initiate radicals to polymerize the sample.

In contrast, at longer wavelengths, such as 385 nm or 400 nm or longer, the S—H bond is typically not cleaved. Accordingly, a photo-initiator is usually needed to generate sufficient free-radicals to polymerize the sample. The choice of the photo-initiator will depend upon, e.g., peak emission wavelength of the light source, the opacity of the sample and its various components, the dimensions of the sample and the desired time required to complete the polymerization reaction or cure.

Non-limiting examples of photo-initiators, which may be used with the present disclosure include acylphosphine oxides such as CIBA® IRGACURE® 819 and/or keto based photo-initiators such as DAROCURE® 1173, each from CIBA Specialty Chemical Company, Basel Switzerland. The amount of photo-initiator employed may affect both the rate and depth of cure. The photo-initiator may be present in the instant sealant composition in an amount of up to 5% based on the total weight of the formulation.

pH Indicator Molecules

The curable sealant compositions of the present disclosure comprise a pH indicator molecule. Generally, pH indicator molecules have physical properties, which change depending upon the pH of the environment to which they are exposed. The pH of the environment may, accordingly, be determined based upon the change. For example, depending upon the pH, the pH indicator molecules may change color and/or change the intensity of absorption and/or emission of light.

The pH indicator molecule is a quantum dot functionalized with a pH-responsive ligand. As used herein, a "quantum dot" or "QD" refers to a semiconductor nanocrystal, which contains anywhere between 100 to 1,000 electrons and ranges in size from about 2-10 nm. The electrons of the quantum dot usually reside in the lowest band of energy levels called the valence band. When the electron absorbs energy it is excited to a higher band of energy levels, called the conduction band, leaving behind an empty spot known as a hole. When the electron returns to the lower valence energy level it emits energy. How far apart the valence band and conduction band are depends upon the size of the particle. The size of the particle controls what is known as the confinement energy. This means that the size of the particle can be used to control the different types of light the particles absorb and emit. When exposed to ultraviolet light, for example, quantum dots may emit any visible color from violet to red (400 nm to 700 nm) depending upon their size, e.g, smaller quantum dots emit blue light while larger quantum dots emit red light. For example, a roughly 2 nm diameter cadmium selenide quantum dot can emit in the blue spectral range (450 nm-496 nm) while an 8 nm diameter quantum cadmium selenide dot particle can emit in the red spectral range (620-750 nm). Quantum dots are well known in the art and are described, for example, in D. Vasudevan, *J. Alloy Comp.* 2015, 636, 395-404.

The quantum dots of the present disclosure comprise an inner core and an outer shell. Non-limiting examples of suitable core materials include cadmium sulfide (CdS), cadmium selenide (CdSe), cadmium telluride (CdTe), zinc sulfide (ZnS), zinc selenide (ZnSe), zinc telluride (ZnTe) and the like, mixtures of such materials, or any other semiconductor or similar materials. Typically, the core material is CdSe.

In some examples, the outer shell may comprise some of the same materials as the core or entirely different materials than the core, and may comprise a semiconductor material. Non-limiting examples of suitable outer shells include cadmium sulfide (CdS), cadmium selenide (CdSe), cadmium telluride (CdTe), zinc sulfide (ZnS), and zinc selenide (ZnSe). Typically, the material of the outer shell comprises CdS, ZnS, or combinations thereof, even more typically the outer shell of the present quantum dots comprise ZnS.

In some examples, a surface of a quantum dot of the present disclosure comprises a stabilizing ligand. In various examples, the stabilizing ligand serves the combined purposes of: 1) passivating electronic states (unsatisfied bonds) associated with atoms at the surface of the nanocrystals; 2) allowing the nanocrystals to be dispersed in a solvent; 3) providing a spatial separation between nanocrystals, given approximately by the length of the ligands, thereby minimizing or regulating the rate of energy transfer among nearby nanocrystals. Stabilizing ligands suitable for use with the quantum dots of the present disclosure include amine chains such as octadecylamine, dodecylamine, and octylamine. Typically, octadecylamine is used.

In some examples, commercially available quantum dots may be used with the present compositions and methods. Suitable commercially available quantum dots include those distributed by, e.g. Sigma-Aldrich, St. Louis Mo., and PlasmChem GmbH, Adlershof, Germany.

The quantum dots used in the present compositions and methods described herein are functionalized with a pH-responsive ligand. As used herein, "functionalized" refers to the addition of functional groups onto the surface of a material by chemical synthesis methods. For example, the pH-responsive ligand may be attached to a surface of a quantum dot by substituting a portion of the stabilizing ligands described herein with a pH-responsive ligand via art known methods such as ligand exchange. In some examples, greater than 50% of the ligands are exchanged, such as greater than 75%, such as up to 100%. See, for example, *Angew. Chem., Int. Ed. Engl.* 1997, 36:145-147. In some examples, the present quantum dots are hydrophobic and retain their hydrophobicity after functionalization with the pH-responsive ligands.

In various examples, one side of a pH-responsive ligand of the present disclosure has an attachment group, e.g., a thiol group, which is attached to a surface of a quantum dot. In some examples, the attachment is a covalent attachment. In various examples, the other side of a pH-responsive ligand of the present disclosure may include a pH-responsive moiety, such as a carboxylic acid, amine or hydroxyl groups.

In some examples, energy transfer between the pH-dependent moiety and the QD (i.e., fluorescence quenching) occurs when the pH-responsive moiety is protonated. In other examples, energy transfer between the pH-dependent moiety and the QD occurs when the pH-responsive moiety is deprotonated. Typically, however, energy transfer between the pH-dependent moiety and the QD occurs when the pH-responsive moiety is protonated. Thus, in various examples, fluorescence remains quenched in a medium, such as the instant curing sealant composition, at an acidic pH; however, as the pH increases, as may occur during curing of the present sealant compositions, the instant pH-responsive moiety is deprotonated, resulting in fluorescence emission.

The fluorescence emission of a QD functionalized with a pH-dependent ligand of the present disclosure is quenched at a pH of less than 6, such as a pH of less than 5, such as a pH of less than 4, such as a pH of less than 3, such as a pH of less than 2.

The instant functionalized quantum dots of the present disclosure are capable of fluorescing over a pH range of approximately 4 to approximately 8, approximately 5 to approximately 7 or approximately 6 to approximately 7.

The range of pH over which the instant functionalized quantum dots is most responsive is determined by the pKa of the pH-dependent moiety. As is known in the art, pKa is defined as the negative base-10 logarithm of the acid dissociation constant of a solution. The lower a $pK_a$ value, the stronger the acid. In general, functionalized QDs that are acid-responsive often contain carboxylic acid groups, while basic pH-responsive quantum dots often contain tertiary amines. The present acidic pH-responsive ligands may, in some examples, have pKa values from about 2.0 to about 6.0. In some examples, the pH-dependent moiety may include a mercaptoalkane carboxylic acid, such as mercaptoacetic acid mercaptooctanoic acid, mercaptohexanoic acid, mercaptodecanoic acid, mercaptopropanoic acid or a combination thereof. The present basic pH-responsive ligands may, in some examples, have pKa values from about 8.0 to about 13.0. In other examples, the basic pH-responsive ligand is a tertiary amine. Examples of suitable tertiary amines include 2-(diethylamino)ethane-1-thiol, 2-(diisopropylamino)ethane-1-thiol, or 2-(dibutylamino)ethane-1-thiol, 2-(pyrrolidin-1-yl)ethane-1-thiol, 2-(piperidin-1-yl)ethane-1-thiol, 2-(dimethylamino)ethane-1-thiol, and combinations thereof.

In some examples, the pH-responsive ligand comprises a mercaptopyridine derivative. Suitable mercaptopyridine derivatives include, but are not limited to 2-mercaptopyridine, 2-mercaptopyridine N-oxide, 4-mercaptopyridine, and combinations thereof.

In some examples, the pH-responsive ligand is hydrophobic. For instance, 3-amino-2-(aminomethyl) propane-1-thiol, 4-aminobenzenethiol, mercaptopyridine derivative, 1-amino-5-methyl-1H-imidazole-2-thiol, 5-amino-2-mercapto-1-me-1H-imidazole-4-carboxan, aminopropane thiol, aminobutane thiol, aminoethane thiol, mercaptoethanol, mercaptopropanol, mercaptobutanol, mercaptoundecanol, or 11-aminoundecane thiol are suitably incorporated into the present compositions. Hydrophobic pH-responsive ligands may be useful for forming a homogenous mixture with the present sealant composition. Combinations of any of the above-described pH-responsive ligands are also contemplated.

Methods

The present disclosure is also directed to a method for determining a sufficient cure state of a composition which comprises a thiol-terminated prepolymer and/or monomers thereof, such as a polythioether or a polysulfide prepolymer and/or monomers thereof, and a curing agent, such as an "ene" crosslinker having a molecular weight in the range of about 100 to about 5000, and, optionally, a photosensitizer as described herein, wherein the method comprises (i) combining the thiol-terminated prepolymer and/or monomer thereof and the "ene" crosslinker with a pH indicator molecule comprising a fluorescent quantum dot functionalized with a pH-responsive ligand and (ii) subjecting a resultant mixture of (i) to curing conditions until the mixture changes its color.

The curing conditions of the present methods are as described herein. Typically, as noted above, a light trigger initiates cure of the sealant formulation. Application of the trigger may take place prior to, at some point during and/or throughout cure of the sealant formulation. The light trigger may also be applied intermittently. The light trigger may be applied by any means known to those skilled in the art at ambient or elevated temperatures.

In the context of the present disclosure the term "sufficient cure" means a curing degree, which is defined by the respective artisan using the method of the disclosure, as he/she desires for the respective application, and can thus vary. Typically, "sufficient cure" is equivalent to "fully cured" or "complete curing", i.e., the curing reaction cannot proceed any further once polymerization is complete.

The pH indicator molecule indicates the extent of curing via a color change during curing. In the instant disclosure, the phrases "extent of curing" or "curing degree" is to be understood as an expression of how far the curing reaction has proceeded between its start (where no reaction at all has taken place) and its end (where the reaction has proceeded as far as possible, the system being fully cured). As noted previously, when the polymerization reaction begins (i.e., cure begins), the acid groups in the present sealant composition begin to be consumed, resulting in a change in pH, for example, to a more neutral or basic pH. Typically, the more acid groups that are consumed, the greater the extent of cure, and the greater change in pH. Hence, the present method directly correlates to the extent of the cure of the composition.

In some examples of the instant methods, the pH indicator molecule as described herein may emit wavelengths, such as 390 nm to 700 nm, of an initially visible first color upon mixing of the (i) thiol-terminated prepolymers and/or monomers thereof, such as polythioether or polysulfide prepolymers and/or monomer thereof and (ii) an "ene" and, optionally, a photosensitizer as also described herein, after illuminating the mixture with visible or ultraviolet light, for example. Subsequently, the pH indicator molecule may then emit wavelengths of a second color during the curing reaction and/or after the curing reaction is complete that is visibly different from the first color.

In other examples, the pH indicator molecule may not emit any fluorescence upon mixing (i) and (ii) and, hence, no color is initially visibly observed, but, as curing progresses, a color becomes observable due to an increase in intensity of emitted fluorescence. For example, no fluorescence may be initially observable, but a green-yellow fluorescence may subsequently appear as curing progresses and/or when the sealant composition is completely cured. Optionally, the pH indicator molecule may emit wavelengths, such as from 390 nm to 700 nm of a visibly noticeable color upon mixing (i) and (ii) and then the fluorescent intensity subsequently decreases as curing progresses. Accordingly, the phrase "changes its color" encompasses any visibly observable color change including changes from no observable color at the initiation of the cure to a visibly noticeable color during and/or at the end of the cure and vice versa.

In some examples, the color change of a sealant composition to be tested ("test composition") for extent of curing will be compared with a reference standard to indicate that curing is complete, e.g., the reference standard may be a sealant composition comprising the same formulation and pH indictor molecule as the test composition, which exhibits a known fluorescence emission intensity and/or color at completion of cure. Cure in the test composition is indicated when the color and fluorescent intensity of the test composition is the same as the color and fluorescent intensity associated with completion of curing in the reference standard. In other examples, variant colors or hues of a single color, e.g., green, will be evident throughout the curing process, indicating that curing of the present sealant composition is ongoing.

In some examples, a pH indicator molecule of the present disclosure may be acid sensitive, e.g., the pH indicator molecules changes color when it registers an increase in pH. Optionally, the pH indicator molecule may be base sensitive and change color when it registers a decrease in pH, for example. Typically, the pH indicator molecule changes color when it registers an increase in pH, e.g. the pH of the present sealant composition increases as the acid groups are consumed during curing.

The pH-responsive ligands, which may be used with the methods of the present disclosure include the mercaptoalkane carboxylic acids, tertiary amines, etc. described herein. These ligands may be attached to quantum dots, such as those described above, and in the following Examples.

Examples

Quantum dots functionalized with pH-responsive ligands were investigated to confirm their ability to detect pH changes in a medium. The materials used in this example are listed in Table 1, below.

As noted in Table 1, CdSe/ZnS core-shell quantum dots (QDs) were purchased from Sigma-Aldrich, St. Louis, Mo. For the first experiment, 1 mg QDs and 45 mg mercaptoacetic acid (MAA) were dissolved in 6 g toluene while being stirred for 16 hours. The solution fluoresced yellow-green under a handheld black light (long wave-length UVA). After the ligand exchange phase, 6 g of 1 M NaOH solution was added to the QD/MAA/toluene solution to deprotonate the quantum dots. A small amount of acetone was then added to the mixture to precipitate out the quantum dots. The mixture was centrifuged for 1 hour at 2000 rpm. The liquid in the test tube was subsequently decanted and the quantum dots were redissolved in 20 g of deionized water. The solution with functionalized QDs continued to fluorescence under long wave UV light (also known as black light), 400 nm to 100 nm. This process was repeated in a second experiment with 3-mercaptopropionic acid (MPA).

Figure 1B:
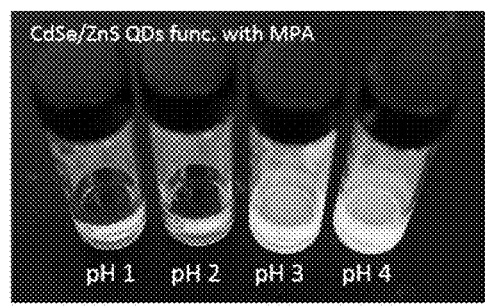

The pH response of the functionalized QDs, which were rendered hydrophilic from the addition of MAA or MPA, was investigated by adding a QD solution to HCl solutions ranging from pH=1 to pH=6. Both types of functionalized QDs continued to fluoresce through pH=3, and did not fluoresce at pH≤2 (FIG. 1).

In view of the above, the use of functionalized quantum dots as fluorescence pH indicator molecules was validated by these experiments. However, for the present sealant compositions, pH-responsive ligands, which result in a color change at higher pH values and do not affect the hydrophobicity of the QDs, will more typically be used with the compositions and methods of the present disclosure.

TABLE 1

Materials

| Material Name | Acronym | CAS # | Sigma-Aldrich Catalog # |
|---|---|---|---|
| CdSe/ZnS core-shell type quantum dots stabilized with octadecylamine ligands, fluorescence λem 540 nm, solid | QDs | N/A | 748056-25MG |
| Mercaptoacetic acid | MAA | 68-11-1 | |
| Mercaptopropionic acid | MPA | 107-96-0 | |
| Toluene | — | 108-88-3 | |
| Sodium hydroxide | NaOH | 1310-73-2 | |
| Acetone | — | 67-64-1 | |

What is claimed is:

1. A curable sealant composition comprising:
   (i) a curable composition comprising at least one thiol-terminated prepolymer, wherein the thiol-terminated prepolymer is selected from the group consisting of a polythioether and a polysulfide and
   a curing agent, wherein the curing agent comprises an "ene" crosslinker; and
   (ii) a pH indicator molecule comprising a quantum dot functionalized with a pH-responsive ligand comprising a pH-responsive moiety,
   wherein energy transfer between the pH-responsive moiety and the quantum dot occurs when the pH-responsive moiety is protonated or deprotonated.

2. The curable sealant composition of claim 1, wherein the quantum dot is a CdSe/ZnS core/shell quantum dot.

3. The curable sealant composition of claim 1, wherein the pH-responsive ligand is protonated.

4. The curable sealant composition of claim 1, wherein the pH-responsive ligand is a tertiary amine.

5. The curable sealant composition of claim 4, wherein the tertiary amine is selected from the group consisting of 2-(diethylamino)ethane-1-thiol, 2-(diisopropylamino)ethane-1-thiol, 2-(dibutylamino)ethane-1-thiol, 2-(pyrrolidin-1-yl)ethane-1-thiol, 2-(piperidin-1-yl)ethane-1-thiol and 2-(dimethylamino)ethane-1-thiol.

6. The curable sealant composition of claim 1, wherein the pH-responsive ligand is a mercaptopyridine derivative.

7. The curable sealant composition of claim 6, wherein the mercaptopyridine derivative is selected from the group consisting of 2-mercaptopyridine, 2-mercaptopyridine N-oxide, and 4-mercaptopyridine.

8. The curable sealant composition of claim 1, wherein the pH-responsive ligand comprises a mercaptoalkane carboxylic acid.

9. The curable sealant composition of claim 8, wherein the mercaptoalkane carboxylic acid is selected from the group consisting of mercaptoacetic acid, mercaptooctanoic acid, mercaptohexanoic acid, mercaptodecanoic acid, mercaptopropanoic acid, and combinations thereof.

10. The curable sealant composition of claim 1, wherein the pH-responsive ligand is hydrophobic.

11. The curable sealant composition of claim 1, further comprising a photosensitizes.

12. The curable sealant composition of claim 1, wherein the polythioether has the following formula (I):

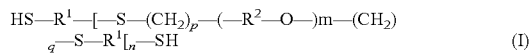
(I)

wherein $R^1$ is a $C_2$-$C_6$ alkyl and $R^2$ is a $C_2$-$C_6$ alkyl;
m is independently selected from a value ranging from 1 to 50;
n is independently selected from a value ranging from 1 to 60;
p is independently selected from a value ranging from 2 to 6; and
q is independently selected from a value ranging from 1 to 5.

13. The curable sealant composition of claim 1, wherein the polysulfide has the following formula:

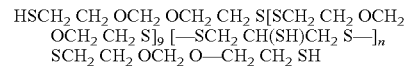

wherein m is from about 5 to about 50, n is from 0 to about 1, and n/m is from about 0.002 to about 0.02, when greater than 0.

14. The curable sealant composition of claim 1, further comprising at least one filler.

15. The curable sealant composition of claim 14, wherein the at least one filler is present in an amount of about 20 to about 40 percent by weight.

16. The curable sealant composition of claim 14, wherein the at least one filler is selected from the group consisting of clay, talc, calcium carbonate, fumed silica, carbon black, plasticizers, solvents, stabilizers, cure accelerators, cure retardants, adhesion promoters, and preservatives.

17. The curable sealant composition of claim 1, further comprising at least one non-polysulfide or non-polythioether prepolymer.

18. The curable sealant composition of claim 1, further comprising at least one non-polysulfide or non-polythioether monomer.

19. The curable sealant composition of claim 1, wherein the "ene" crosslinker is selected from the group consisting of diethylene glycol divinyl ether, 1,4-cyclohexanedimethanol divinyl ether, 1,3,5-triallyl-1,3,5-triazine-2,4,6(1H,3H,5H)-trione, 1,4-butanediol diacrylate, bisphenol A bimethacrylate, 1,3,5-triacryloylhexahydro-1,3,5-triazine, and pentaerythritol tetraacrylate.

20. The curable sealant composition of claim 1, wherein the "ene" crosslinker ranges from 0.7 to 1.5 moles per mole of thiol in the at least one thiol-terminated prepolymer.

* * * * *

UNITED STATES PATENT AND TRADEMARK OFFICE
CERTIFICATE OF CORRECTION

PATENT NO. : 10,246,557 B2
APPLICATION NO. : 14/955388
DATED : April 2, 2019
INVENTOR(S) : Katherine L. Frank and Andrew M. Zweig Page 1 of 1

It is certified that error appears in the above-identified patent and that said Letters Patent is hereby corrected as shown below:

In the Claims

Column 14, Line 5, Claim 13 delete:
"HSCH$_2$ CH$_2$ OCH$_2$ OCH$_2$ CH$_2$ S[SCH$_2$ CH$_2$ OCH$_2$ OCH$_2$ CH$_2$ S]$_9$ [—SCH$_2$ CH(SH)CH$_2$ S—]$_n$ SCH$_2$ CH$_2$ OCH$_2$ O—CH$_2$ CH$_2$ SH",
And insert therefor:
--HSCH$_2$ CH$_2$ OCH$_2$ OCH$_2$ CH$_2$ S[SCH$_2$ CH$_2$ OCH$_2$ OCH$_2$ CH$_2$ S]$_m$ [—SCH$_2$ CH(SH)CH$_2$ S—]$_n$ SCH$_2$ CH$_2$ OCH$_2$ O—CH$_2$ CH$_2$ SH--.

Signed and Sealed this
Twenty-second Day of October, 2019

Andrei Iancu
*Director of the United States Patent and Trademark Office*